United States Patent
Liang et al.

(10) Patent No.: US 10,499,846 B2
(45) Date of Patent: Dec. 10, 2019

(54) EOG-BASED SLEEP STAGING METHOD, COMPUTER PROGRAM PRODUCT WITH STORED PROGRAMS, COMPUTER READABLE MEDIUM WITH STORED PROGRAMS, AND ELECTRONIC APPARATUSES

(71) Applicant: NATIONAL CHENG KUNG UNIVERSITY, Tainan (TW)

(72) Inventors: Sheng-Fu Liang, Tainan (TW); Chih-En Kuo, Tainan (TW); Yu-Hung Li, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 610 days.

(21) Appl. No.: 15/176,141

(22) Filed: Jun. 7, 2016

(65) Prior Publication Data
US 2017/0347947 A1 Dec. 7, 2017

(51) Int. Cl.
*A61B 5/00* (2006.01)
*A61B 3/113* (2006.01)
*A61B 5/0496* (2006.01)

(52) U.S. Cl.
CPC ............ *A61B 5/4812* (2013.01); *A61B 3/113* (2013.01); *A61B 5/0496* (2013.01);
(Continued)

(58) Field of Classification Search
CPC ... A61B 5/4812; A61B 5/4815; A61B 5/4809; A61B 5/4806; A61B 5/0496;
(Continued)

(56) References Cited

U.S. PATENT DOCUMENTS

| | | | |
|---|---|---|---|
| 6,805,668 B1* | 10/2004 | Cadwell | A61B 5/16 600/300 |
| 2008/0154111 A1* | 6/2008 | Wu | A61B 5/0478 600/383 |

(Continued)

OTHER PUBLICATIONS

Chun-Yu Chen, "A heart-rate-variability based automatic sleep scoring method," A thesis submitted to the graduate division in partial fulfillment of requirements for degree of master in Institute of Medical Informatics, Nation Cheng Kung University, Tainan, Taiwan, R.O.C., Jun. 2012.
(Continued)

*Primary Examiner* — Matthew Kremer
*Assistant Examiner* — Avery M Foley
(74) *Attorney, Agent, or Firm* — CKC & Partners Co., LLC (57) ABSTRACT

This invention mainly discloses an EOG-based sleep staging method which is used to improve of an accuracy of automatic sleep judging result. The method may be executed by a processor and comprises steps of reading a to-be-test data having a variation depending on time of EOG generated by a user during a sleep process; acquiring a plurality of eye movement characteristics based on a variation of the EOG of a period, with the characteristics including an eye movement ratio, a blink count, a low frequency power ratio, a high frequency power ratio, an alpha rhythm ratio, a spindle rhythm ratio, a delta rhythm ratio and an average amplitude of eletrooculogram (EOG) signals; and determining a sleep state of the period is a "WAKE stage", a "REM stage", a "S1 stage", a "S2 stage", or a "SWS stage" based on the EOG characteristics. Furthermore, a computer readable medium with stored programs, and electronic apparatuses are provided.

10 Claims, 7 Drawing Sheets

(52) U.S. Cl.
CPC .......... *A61B 5/7225* (2013.01); *A61B 5/7246* (2013.01); *A61B 5/7264* (2013.01); *A61B 5/7278* (2013.01)

(58) Field of Classification Search
CPC ... A61B 5/7225; A61B 5/7228; A61B 5/7214; A61B 5/72; A61B 5/7246; A61B 5/7264; A61B 5/7278; A61B 3/113
See application file for complete search history.

(56) References Cited

U.S. PATENT DOCUMENTS

| | | | |
|---|---|---|---|
| 2013/0165760 A1* | 6/2013 | Erlinger | A61B 5/04 600/382 |
| 2015/0190086 A1* | 7/2015 | Chan | A61B 5/4812 600/301 |
| 2015/0245800 A1* | 9/2015 | Sorensen | A61B 5/7264 600/558 |

OTHER PUBLICATIONS

Fazil Duman et al., "Efficient sleep spindle detection algorithm with decision tree," Expert Systems with Applications 36 (2009) 9980-9985.

Bruno Jammes et al., "Automatic EOG analysis: A first step toward automatic drowsiness scoring during wake-sleep transitions," Somnologie 12:227-232 (2008).

\* cited by examiner

Time (minute)

EOG-BASED SLEEP STAGING METHOD, COMPUTER PROGRAM PRODUCT WITH STORED PROGRAMS, COMPUTER READABLE MEDIUM WITH STORED PROGRAMS, AND ELECTRONIC APPARATUSES

BACKGROUND

Field of Invention

The present invention relates to a sleep staging method. More particularly, the present invention relates to an electrooculograppy(EOG)-based sleep staging method, a computer readable medium storing a program, and an electronic device.

Description of Related Art

Sleep is related to metabolism and memory consolidation. Long-term bad sleep quality may cause physical and psychological problems such as dyssomnia, and person having severe conditions may seek for medical diagnosis for the sleep problem.

Figure 1:
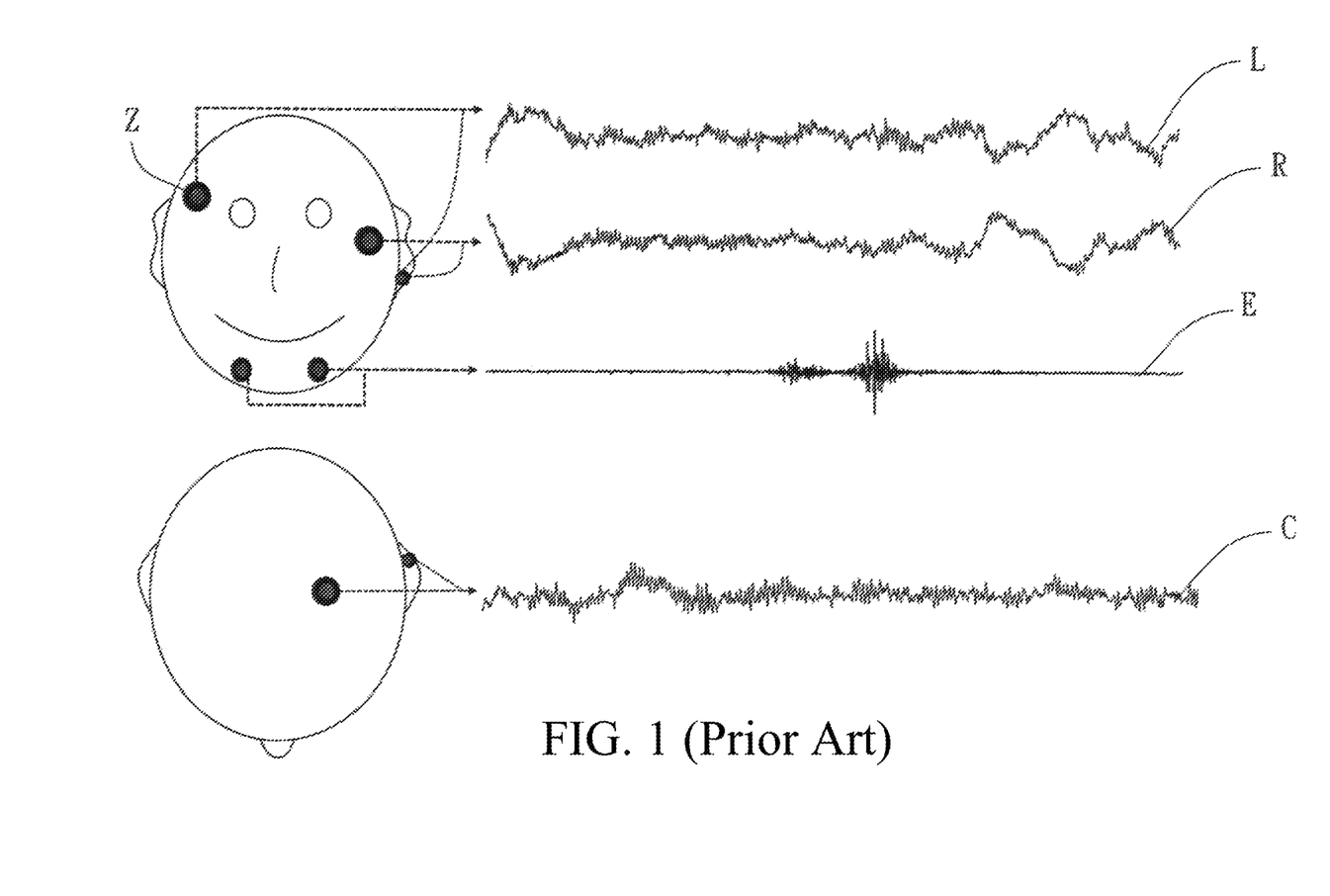
FIG. 1 is a schematic diagram illustrating electrodes and signals when recording EEG, EMG and EOG using multi-channel polysomnography in the prior art.

In conventional sleep diagnosis and treatment, multi-channel polysomnography (PSG) recording is often used to record physiological signals such as electroencephalography (EEG), electromyography (EMG), and electrooculography (EOG). For example, as shown in FIG. 1, a left EOG signal L, a right EOG signal R, an EMG signal E, and an EEG signal C are acquired by electrodes Z disposed on the left canthus, the right canthus, the chin, and the top of the head respectively for medical personnel to score different stages during sleep such as WAKE stage, rapid eye movement (REM) stage, S1 stage, S2 stage, slow-wave sleep (SWS) stage, and so on in order to understand the sleep problem and to provide suggestions.

Figure 2A:
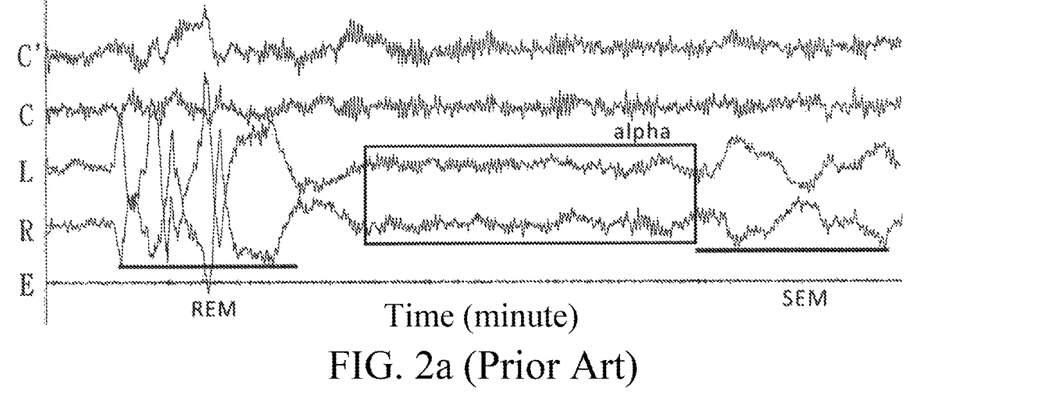
FIG. 2a is a diagram illustrating the EOG signals of a user in certain sleep states.
Figure 2B:
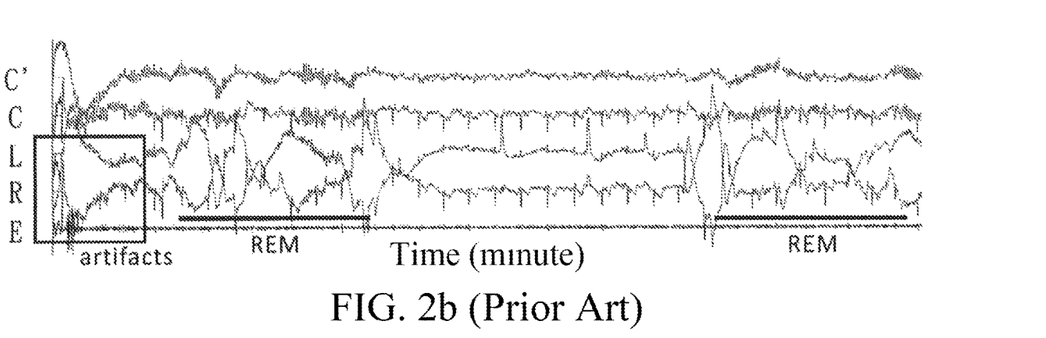
FIG. 2b is a diagram illustrating the EOG signals of a user in certain sleep states.
Figure 2C:
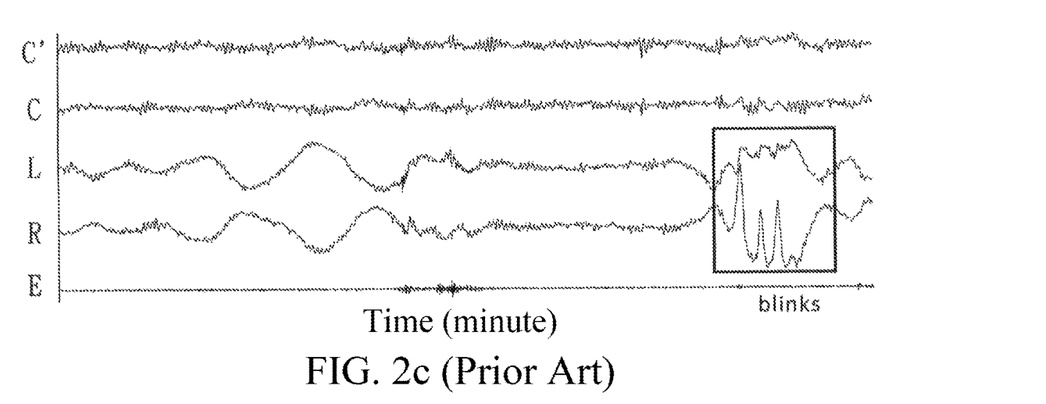
FIG. 2c is a diagram illustrating the EOG signals of a user in certain sleep states.
Figure 2D:
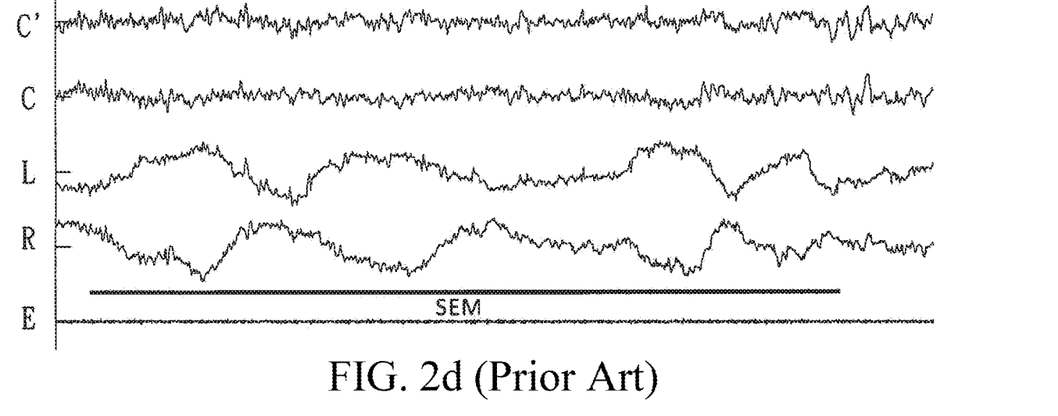
FIG. 2d is a diagram illustrating the EOG signals of a user in certain sleep states.
Figure 2E:
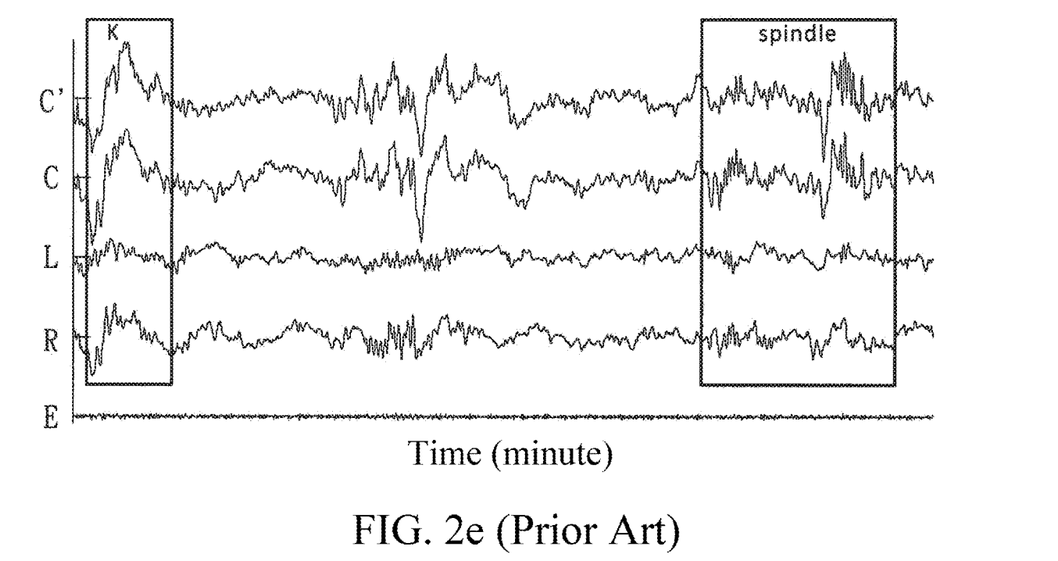
FIG. 2e is a diagram illustrating the EOG signals of a user in certain sleep states.
Figure 2F:
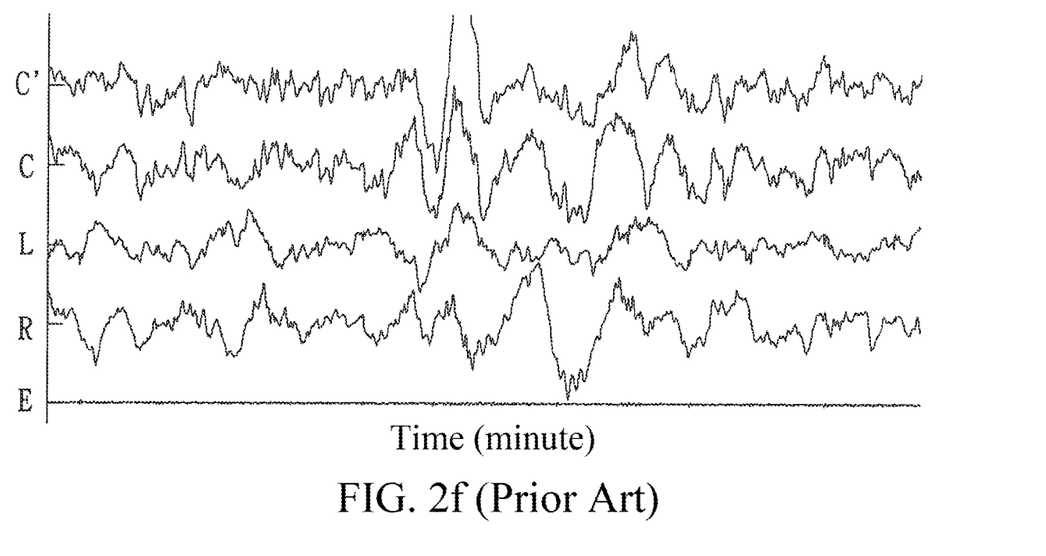
FIG. 2f is a diagram illustrating the EOG signals of a user in certain sleep states.
Figure 2G:
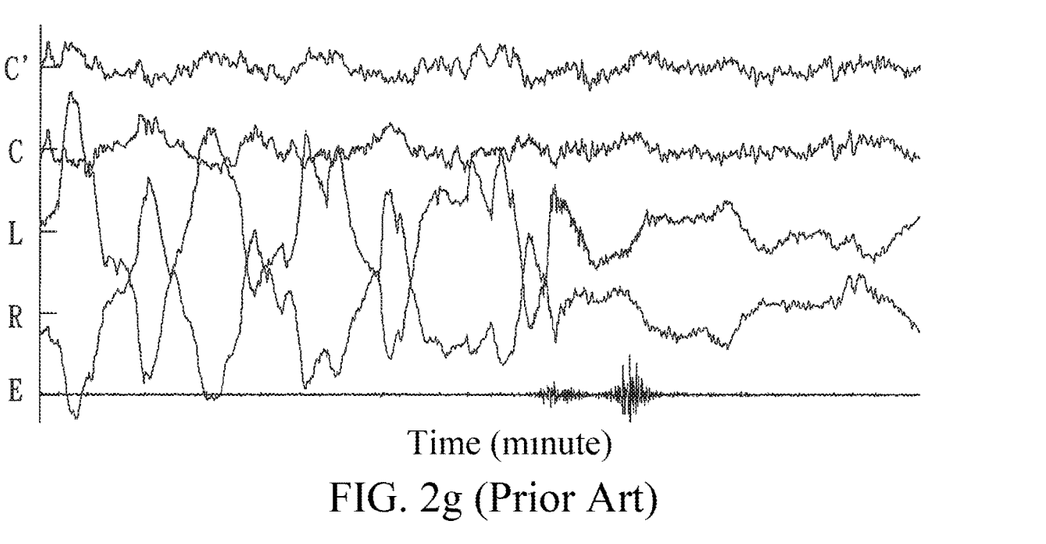
FIG. 2g is a diagram illustrating the EOG signals of a user in certain sleep states.

Take EOG as an example, referring to EOG signals during sleep in FIG. 2a to FIG. 2g. C and C' represent the EEG signals. E represent the EMG signal. L and R represent the left EOG and the right EOG respectively, in which the phase of the signal L is inverted from the phase of the signal R. In FIG. 2a, REM stage (<6 Hz) and alpha rhythm (8-13 Hz) can be scored. In FIG. 2b, REM stage and artifacts from EEG can be scored. Blinks can be scored in FIG. 2c. First stage in SEM stage (0.2-0.6 Hz) can be scored in FIG. 2d. Spindle and K-complexes can be scored in FIG. 2e. SWS stage (a low-frequency high-amplitude wave within 0-4 Hz) can be scored in FIG. 2f, in which EOG is synchronized with EEG. REM stage can be scored in FIG. 2g.

However, the manual scoring approach is time-consuming and is liable to misjudge. In addition, factors such as locations and testing approaches may cause disturbance to the sleep quality of the subject during the recording process. Therefore, the scoring result may not precisely reflect the real sleep condition of the subject, and thus it's required to develop a "low-disturbance sleep staging method".

Heart rate (i.e. frequency of heart beats) signals have characteristics such as "low-disturbance to the user", "complete sleep period is sensed" and "easily recorded", and therefore it has been developed a sleep staging method using heat rate as disclosed in Chun-Yu CHEN, "A heart-rate-variability based automatic sleep scoring method," which is a thesis submitted to the graduate division in partial fulfillment of requirements for degree of master in Institute of Medical Informatics, Nation Cheng Kung University, Tainan, Taiwan, R.O.C., June, 2012. However, different people may have same heart rate characteristics. For example, a heat rate of an athlete with good cardiopulmonary function is generally lower than that of normal people, and accordingly the scoring accuracy for staging sleep is affected (about 70%). Therefore, it is still necessary to develop other automatic sleep scoring technology.

In view of this, it is necessary to improve the above disadvantages of the prior art, in order to meet the actual needs and enhance its usefulness.

SUMMARY

The invention provides an EOG-based sleep staging method which is capable of increasing the scoring accuracy.

The invention also provides a non-transitory computer readable recording medium storing a program, and the program is loaded and executed by a computer for increasing the scoring accuracy.

The invention also provides an electronic which is capable of loading and executing a computer program for increasing the scoring accuracy of sleep staging.

The invention provides an electrooculograppy(EOG)-based sleep staging method for a processor. The method includes: a preparing step, reading to-be-test data, wherein the to-be-test data includes a EOG signal having a variation depending on time of the EOG signal generated by a user during a sleep process; an acquiring step, acquiring eye movement characteristics according to the variation of the EOG signal during an epoch, wherein the eye movement characteristics comprise an eye movement ratio, a blink count, a low-frequency power ratio, a high-frequency power ratio, an alpha ratio, a spindle ratio, a delta ratio and an mean amplitude of the EOG signal; and a determining step, determining a sleep state of the epoch is a WAKE stage, a non-rapid-eye-movement (REM) stage, a S1 stage a S2 stage or a slow-wave-sleep (SWS) stage according to the plurality of eye movement characteristics.

The sleep state is determined by a decision tree in the determining step, and the decision tree includes: a first node, determining whether the eye movement ratio is greater than a first threshold, and performing a second node if yes, and performing a third node if not; the second node, determining whether the delta ratio is greater than a second threshold and the high-frequency power ratio is less than a third threshold, and determining that the sleep state is the SWS stage if yes, and determining that the sleep state is the S2 stage if not; the third node, determining whether the eye movement ratio is greater than a fourth threshold, and performing a fourth node if yes, and performing a fifth node if not, wherein the fourth threshold less than the first threshold; the fourth node, determining whether the spindle ratio is greater than a fifth threshold and the low-frequency power ratio is less than a sixth threshold, and performing a sixth node if yes, and determining that the sleep state is the REM stage if not; the fifth node, determining whether the alpha ratio is greater than a seventh threshold and the blink count is greater than an eighth threshold, and determining that the sleep state is the WAKE stage if yes, and performing a seventh node if not; the sixth node, determining whether the mean amplitude of the EOG signal is greater than a ninth threshold, and determining that the sleep state is the S1 stage if yes, and determining that the sleep state is the S2 stage if not; and the seventh node, determining whether the alpha ratio is greater than a tenth threshold, and determining that the sleep state is the S2 stage if yes, and determining that the sleep state is the REM stage if not, wherein the tenth threshold is less than the seventh threshold.

The first threshold is ranged from 0.55 to 0.65, the second threshold is ranged from 0.19 to 0.25, the third threshold is ranged from 0.01 to 0.05, the fourth threshold is ranged from 0.3 to 0.5, the fifth threshold is ranged from 0.2 to 0.4, the sixth threshold is ranged from 0.12 to 0.19, the seventh threshold is ranged from 0.3 to 0.5, the eighth threshold is ranged from 4 to 6, the ninth threshold is ranged from 0.25 to 0.35, the tenth threshold is ranged from 0.12 to 0.19.

The EOG signal includes a left EOG signal and a right EOG signal, and the method further includes: calculating a correlation coefficient between the left EOG signal and the right EOG signal in the epoch as the eye movement ratio.

Before calculating the correlation coefficient, the method further includes: performing a 0-6 hertz and four-order band pass filter on the left EOG signal and the right EOG signal.

The method further includes: selecting one of the left EOG signal and the right EOG signal as a sampling signal, calculating an EOG velocity according to the sampling signal, and counting times of the EOG velocity being greater than a threshold in the epoch as the blink count.

The EOG velocity is calculated by a formula:

$$V = \frac{dEOG}{dt} \approx \frac{EOG((k+1) \cdot T) - EOG(k \cdot t)}{T},$$

where V is the EOG velocity;

$\frac{dEOG}{dt}$ is a first derivative function of the sampling signal with respect to time t; T is a sampling period; $EOG(k \cdot T)$ is the sampling signal in a $k^{th}$ sampling period; and $EOG((k+1) \cdot T)$ is the sampling signal in a $(k+1)^{th}$ sampling period.

The method further includes: transforming the sampling signal into a frequency-domain signal, and calculating a ratio of 0-4 hertz of the frequency-domain signal to 0-30 hertz of the frequency-domain signal in the epoch as the low-frequency power ratio; calculating a ratio of 13-22 hertz of the frequency-domain signal to 0-30 hertz of the frequency-domain signal in the epoch as the high-frequency power ratio; calculating a ratio of an alpha rhythm to the sampling signal in the epoch as the alpha ratio; calculating a ratio of a spindle to the sampling signal in the epoch as the spindle ratio; calculating a ratio of a delta wave to the sampling signal in the epoch as the delta ratio.

The method further includes: calculating a mean of absolute amplitudes of the left EOG signal and right EOG signal as the mean amplitude of EOG signal.

A normalization step is performed between the acquiring step and the determining step, and the normalization step includes: sequentially taking the eye movement ratio, the blink count, the low-frequency power ratio, the high-frequency power ratio, the alpha ratio, the spindle ratio, the delta ratio and the mean amplitude of EOG signal as a normalization target; sorting values of the normalization target, uniformly dividing the values into ten levels, calculating a mean of the values in a highest level of the levels as a high standard value, and calculating a mean of the values in a lowest level of the levels as a low standard value; and setting the low standard value as 0, and setting the high standard value as 1, such that all the values of the normalization target is ranged from 0 to 1.

The invention provides a non-transitory computer readable recording medium storing a program, wherein the program is configured to be loaded and executed by a computer to perform the aforementioned method.

The invention provides an electronic device configured to load a program stored in a computer readable recording medium for performing the aforementioned method.

In the EOG-based sleep staging method, the non-transitory computer readable recording medium, and the electronic device described above, the sleep state of the epoch is determined, by the decision three, as the WAKE stage, the REM stage, the S1 stage, the S2 stage or the slow-wave-sleep (SWS) stage in the epoch according to the eye movement characteristics. Accordingly, an advantage of "easy to get accurate sleep staging result" is achieved, and it can be applied to fields such as clinical medicine and home health care.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings so that the object described above, features and advantages of the present invention can be better understood.

The term "EOG signal" used in the specification represents electrical signals generated by the eye movements in everyday life. For example, different electric signals generated around eyelids can be sensed through electrodes during a sleep stage such as WAKE stage, REM stage, S1 stage, S2 stage and SWS stage. But the invention is not limited thereto, and the term should be understood by people in the art.

The term "eye movement ratio" represents a ratio between activities of the two eyes and is calculated according to two EOG signals. The term should be understood by people in the art.

The term "blink count" represent times of one eye blinks detected according to an EOG signal. The term should be understood by people in the art.

The term "low-frequency power ratio" represent a ratio of 0-4 Hz to 0-30 Hz calculated according to an EOG signal. The term should be understood by people in the art.

The term "high-frequency power ratio" represent a ratio of 13-22 Hz to 0-30 Hz calculated according to an EOG signal. The term should be understood by people in the art.

The term "alpha ratio" represents a ratio of an alpha rhythm to an EOG signal. The term should be understood by people in the art.

The term "spindle ratio" represents a ratio of a spindle to an EOG signal. The term should be understood by people in the art.

The term "delta ratio" represents a ratio of a delta wave to an EOG signal. The term should be understood by people in the art.

The term "mean amplitude of EOG signal" represents the mean of the amplitudes of two EOG signals within a specific time period (e.g. window). The term should be understood by people in the art.

Figure 3:
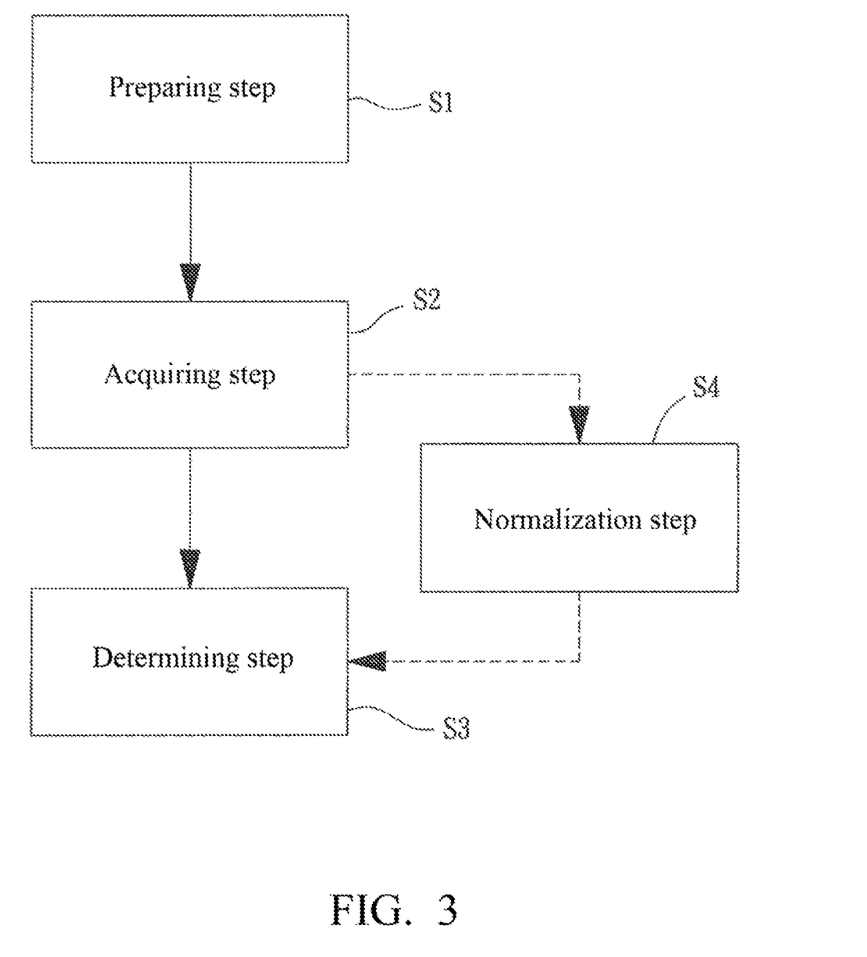
FIG. 3 is a diagram illustrating a flow char of an EOG-based sleep staging method according to an embodiment of the invention.

Referring to FIG. 3, FIG. 3 is a diagram illustrating a flow chart of an EOG-based sleep staging method according to an embodiment of the invention. The EOG-based sleep staging method is executed by a computer system. In the embodiment, the computer system has a processor for executing a sleep staging program as an implementation to perform the EOG-based sleep staging method, but the invention is not limited thereto. The EOG-based sleep staging method includes a preparing step S1, an acquiring step S2 and a determining step S3, and they will be described below.

Referring to FIG. 3, in the preparing step S1, to-be-test data is read. The to-be-test data includes an EOG signal having a variation depending on time of the EOG signal generated by a user during a sleep process. In the embodiment, EOG signals of left-eye channel and right-eye channel (e.g. the signals sensed from the left canthus and the right canthus in FIG. 1) during the sleep process may be acquired by a user using a measurement device (e.g. multi-channel PSG) before sleep. The EOG signals are digital signals having sampling frequency of 1K hertz (Hz) and resolution of 16-bits. The EOG signals are first down sampled to 128 Hz. In addition, frequency from 0.5 Hz to 35 Hz are extracted from the EOG signals. For example, a band-pass filter is performed on the EOG signals. Then, each EOG signal is divided into multiple non-overlapping segments by interval of 2 seconds to perform a 256-point fast fourier transform (FFT). Then, fifteen 2-second segments in frequency domain are taken as an 30-second epoch for the convenience of subsequent process, but the invention is not limited thereto.

Referring to FIG. 3, in the acquiring step S2, multiple eye movement characteristics are acquired according to the variation of the EOG signal during an epoch. The eye movement characteristics include an eye movement ratio, a blink count, a low-frequency power ratio, a high-frequency power ratio, an alpha (α) ratio, a spindle ratio, a delta (δ) ratio and an mean amplitude of EOG signal. Examples are provided below to describe the eye movement characteristics.

TABLE 1

Eye movement characteristics comparison

| Symbol | Type | Feature | Source |
|---|---|---|---|
| M | Eye movement ratio | Ratio of activities between the two eyes | Left-eye channel (LEOG) and right-eye channel (REOG) |
| B | Blink count | Times of one eye blinks | LEOG |
| $R_{P0-4}$ | Low-frequency power ratio | Ratio of 0-4 Hz to 0-30 Hz | REOG |
| $R_{P13-22}$ | High-frequency power ratio | Ratio of 13-22 Hz to 0-30 Hz | REOG |
| $R_\alpha$ | Alpha ratio | Ratio of alpha rhythm | REOG |
| $R_S$ | Spindle ratio | Ratio of spindle | REOG and LEOG |
| $R_\delta$ | Delta ratio | Ratio of delta wave | REOG |
| A | Mean amplitude of EOG | Mea amplitudes of the signals within a widow | REOG and LEOG |

For example, referring to Table 1 together, the calculation of the eye movement ratio M is first described. Since the eye movement activities shows opposed-phase signals in left and right eye EOG channel, a correlation coefficient between the signals can be taken as an important characteristic in order to separate major eye movement stages (e.g. WAKE, REM and S1 stages) from the rest (e.g. S2, and SWS stages). The samples of the left EOG signal and the right EOG signal are denoted as $\{x_1, x_2, \ldots, x_n\}$ and $\{y_1, y_2, \ldots, y_n\}$ respectively, and the means thereof are $\bar{x}$ and $\bar{y}$ respectively, and the standard deviations thereof are $S_x$ and $S_y$ respectively. The covariance $S_{xy}$ of the two sets of samples is defined as a following formula (1a):

$$S_{xy} = \frac{1}{n-1}\sum_{i=1}^{n}(x_i - \bar{x})(y_i - \bar{y}) \qquad (1a)$$

Therefore, the correlation coefficient r can be defined as a following formula (1b):

$$r = \frac{S_{xy}}{S_x S_y} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \qquad (1b)$$

The correlation coefficient r is used to represent the degree of the correlation between the two sets of samples, and the value thereof is ranged from −1 to +1.

In addition, a two second window is designed to detect major eye movements in an epoch. A fourth-order 0-6 Hz band pass filter such as Butterworth filter is performed on the left EOG signal and right EOG signal to eliminate the EEG artifacts and to preserve usable eye movement characteristics. Then, the correlation coefficient between the left and the right EOG signals is detected by using a threshold and counted. If the correlation coefficient is lower than the threshold, then the time dot (i.e. window) is determined as an eye moving segment.

The calculation of the blink count B is described herein. Because eye blinking is a common eye movement type which could be found mostly in WAKE stage, eye blinking numbers are counted in one epoch as a characteristic to detect the suddenly wake up in the night and correct the missed wake epoch. The blink detection algorithm includes steps of: (i) a fourth-order 0-6 Hz band pass filter such as Butterworth filter is performed on the right EOG signal (also referred to a sampling signal) to eliminate high frequency noises and the artifacts from EGG and to preserve usable eye movement characteristics; (ii) an EOG velocity is calculated according to the sampling signal by a first-order approximation as shown in a following formula (2):

$$V = \frac{dEOG}{dt} \approx \frac{EOG((k+1) \cdot T) - EOG(k \cdot t)}{T} \quad (2)$$

V is the EOG velocity.

$\frac{dEOG}{dt}$ is a first derivative function of the sampling signal with respect to time t. T is a sampling period. EOG(k·T) is the sampling signal in a $k^{th}$ sampling period. EOG((k+1)·T) is the sampling signal in a (k+1) sampling period. The blink detection algorithm also includes a step (iii): times of the EOG velocity being greater than a threshold in the epoch are counted as the blink count. For example, a closing velocity followed by a period of opening velocity is found. The two velocities should exceeds a given threshold, and the event duration has to last lass then 0.5 seconds. If the peek amplitude is greater than the given threshold, then it is taken as a blink to calculate the blink count B. The definition of eye opening and eye closing should be understood by people in the art by referring to a reference such as Jammes, B., Sharabty, H., & Esteve, D. (2008). "Automatic EOG analysis: A first step toward automatic drowsiness scoring during wake-sleep transitions", Somnologie-Schlafforschung und Schlafmedizin, 12(3), 227-232, and therefore it will not be described herein.

The power ratio, such as the frequency power ratio Ro and the high-frequency power ratio $R_{P13-22}$ of the EOG signal is described herein. After the FFT, frequency spectrums corresponding to the 15 2-second segments are averaged to represent the spectrum for a 30-second epoch. Therefore, a ratio of each band to the total power of 0-30 Hz is calculated as a characteristic as shown in a following formula (3).

$$PR = \frac{\sum_{f=i}^{j} PS(f)}{\sum_{f=0}^{30} PS(f)} \quad (3)$$

In the formula (3), i and j are a lower bound and an upper bound of a particular band respectively. Accordingly, 0-4 Hz may be defined as a low frequency band, and 13-22 Hz is defined as a high-frequency band. A ratio of 0-4 Hz to 0-30 Hz in the same epoch is calculated as the low-frequency power ratio $R_{P0-4}$. In addition, a ratio of 13-22 Hz to 0-30 Hz in the same epoch is calculated as the high-frequency power ratio $R_{P13-22}$.

Other ratios, such as alpha ratio $R_\alpha$, spindle ratio $R_S$, and delta ratio $R_\delta$, of the EOG signal are described herein. The alpha ratio $R_\alpha$ is a ratio of the alpha windows to the total windows in an epoch. Two eighth-order band-pass Butterworth filters (e.g. 8-13 Hz, and 22-30 Hz) may be used. Besides the conventional alpha band of 8-13 Hz, a beta band of 22-33 Hz is also added as a characteristic because the WAKE stage has high power in the 22-30 Hz band. After performing the two filters, the two signals can be combined, and a threshold (e.g. 0.5) is used to detect it. If the value of the absolute amplitude of the combined signal relative to the original signal is greater than the threshold, then the time dot (i.e. window) is determined as alpha rhythm.

The spindle ratio $R_S$ is a ratio of spindle windows to the total windows in an epoch. FFT and Butterworth band pass filtering among the sigma band of 12-15 Hz are used to calculate the spindle ratio. The FFT is used to find whether the power of the sigma band (i.e. 12-15 Hz) is high, and the filtered signal is used to detect any large sudden amplitude changes. If both are high, the time dot (i.e. window) is determined as spindle, and people in the art should be able to understand the disclosure herein by referring to related references such as Duman, F., Erdamar, A., Erogul, O., Telatar, Z., & Yetkin, S. (2009). Efficient sleep spindle detection algorithm with decision tree. Expert Systems with Applications, 36(6), 9980-9985, and it will not be described in detail herein.

Similar to the alpha ratio $R_\alpha$ and the spindle ratio $R_S$, the delta ratio $R_\delta$ is a ratio of SWS windows to the total windows in an epoch. A third-order 0.5-2 Hz Butterworth band pass filter may be used. If the amplitude of the filtered signal is greater than a threshold (e.g. 0.2), then the time dot (i.e. window) is determined as SWS. Therefore, the SWS stage is separated from other stages.

The calculation of the mean amplitude of EOG signals is described herein. A mean of absolute amplitudes of total data points of the left EOG signal and right EOG signal is calculated as a characteristic. The energy of the EOG signal in the WAKE stage and the S1 stage is higher than that of the S2 stage and the SWS stage.

Referring to FIG. 3, in the determining step S3, a sleep stage of the user in the epoch is determined as the WAKE stage P1, the REM stage P2, the S1 stage P3, the S2 stage P4 or the SWS stage P5 according to the eye movement ratio M, the blink count B, the low-frequency power ratio $R_{P0-4}$, the high-frequency power ratio $R_{P13-22}$, the alpha ratio $R_\alpha$, the spindle ratio $R_S$, the delta ratio $R_\delta$ and the mean amplitude of EOG. The determining step S3 may be performed by decision tree to determine the sleep state as described below.

Figure 4:
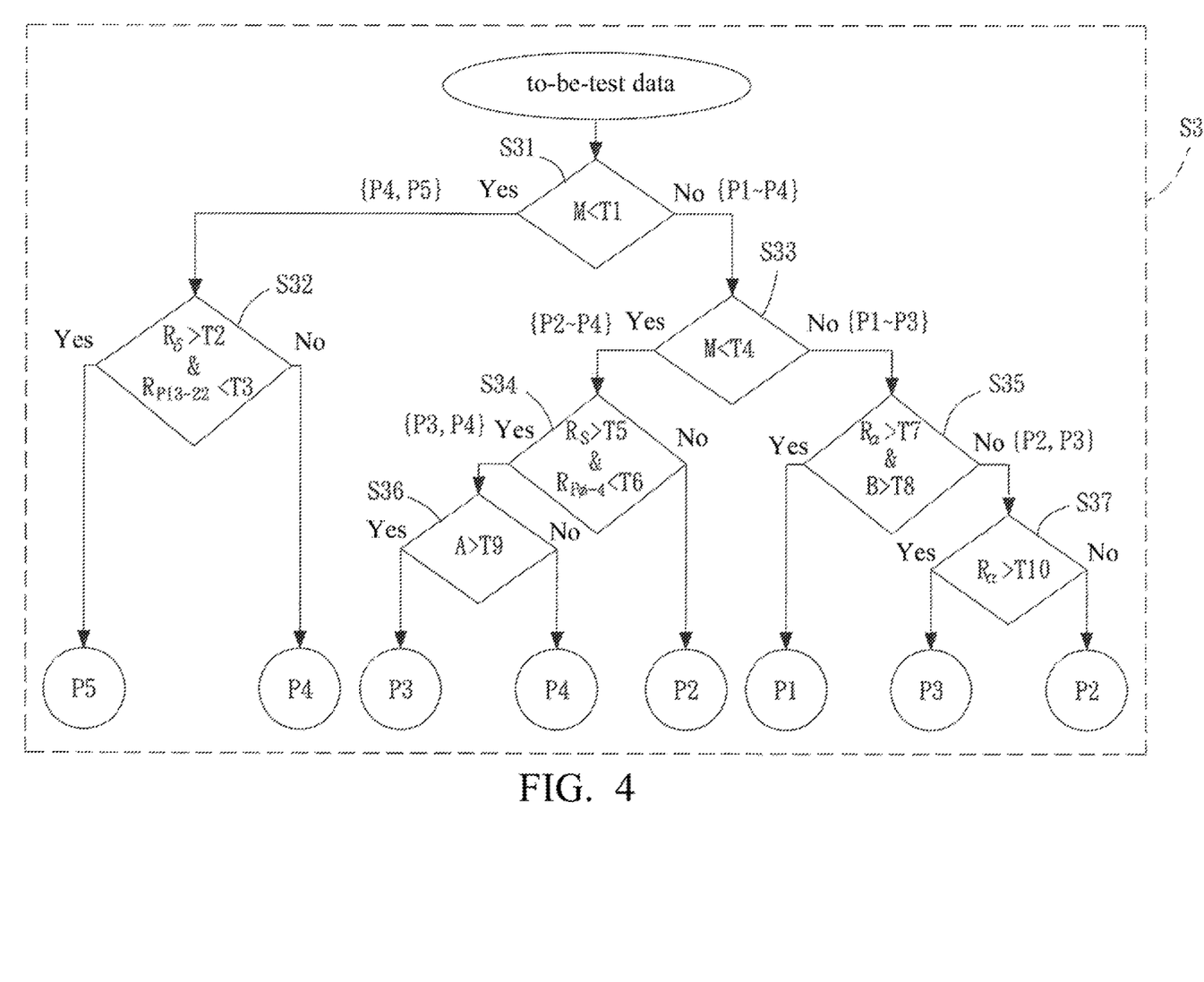
FIG. 4 is a schematic diagram illustrating a decision tree of a determining step according to the invention.

Referring to FIG. 4, FIG. 4 is a schematic diagram illustrating a decision tree of a determining step according to the invention. The decision tree used in the determining step S3 includes a first node S31, a second node S32, a third node S33, a fourth node S34, a fifth node S35, a sixth node S36 and a seventh node S37. In the first node S31, whether the eye movement ratio M is greater than a first threshold T1 is determined; if yes, the second stage S32 is performed; and if not, the third node S33 is performed. In the second node S32, whether delta ratio $R_a$ is greater than a second threshold T2 and the high-frequency power ratio $R_{P13-22}$ is less than a third threshold T3 are determined; if yes, the sleep state is determined as the SWS stage P4; and if not, the sleep state is determined as the S2 stage P3. In the third node S33, whether the eye movement ratio M is greater than a fourth threshold T4 is determined; if yes, the fourth node S34 is performed; and if not, the fifth node S35 is performed. The fourth threshold T4 is less than the first threshold T1. In the fourth node S34, whether the spindle ratio $R_S$ is greater than a fifth threshold T5 and the low-frequency power ratio $R_{P0-4}$ is less than a sixth threshold T6 are determined; if yes, the sixth node S36 is performed; and if not, the sleep state is determined as the REM stage P5. In the fifth node S35, whether the alpha ratio $R_\alpha$ is greater than a seventh threshold T7 and the blink count B is greater than an eighth threshold T8 are determined; if yes, the sleep state is determined as the WAKE stage P1; and if not, the seventh node S37 is performed. In the sixth node S36, whether the mean amplitude of EOG signal is greater than a ninth threshold T9 is determined; if yes, the sleep stage is determined as the S1 stage P2; and if not, the sleep state is determined as the S2 stage P3. In the seventh node S37, whether the alpha ratio $R_\alpha$ is greater than a tenth threshold T10 is determined; if yes, the sleep state is determined as the S2 stage P3; and if not, the sleep state is determined as the REM stage P5. The tenth threshold T10 is less than the seventh threshold T7.

In the embodiment, the first threshold T1 is ranged from 0.55 to 0.65, the second threshold T2 is ranged from 0.19 to 0.25, the third threshold T3 is ranged from 0.01 to 0.05, the fourth threshold T4 is ranged from 0.3 to 0.5, the fifth threshold T5 is ranged from 0.2 to 0.4, the sixth threshold T6 is ranged from 0.12 to 0.19, the seventh threshold T7 is ranged from 0.3 to 0.5, the eighth threshold T8 is ranged from 4 to 6, the ninth threshold T9 is ranged from 0.25 to 0.35, and the tenth threshold T10 is ranged from 0.12 to 0.19, but the invention is not limited thereto.

Referring to FIG. 3 again, in some embodiments of the EOG-based sleep staging method of the invention, a normalization step S4 is performed after the acquiring step S2 and before the determining step S3. In the normalization step S4, the eye movement ratio M, the blink count B, the low-frequency power ratio $R_{P0-4}$, the high-frequency power ratio $R_{P13-22}$, the alpha ratio $R_\alpha$, the spindle ratio $R_S$, the delta ratio $R_\delta$ and the mean amplitude of EOG signal are sequentially taken as a normalization target. Values of the normalization target are sorted. The values are uniformly divided into ten levels. A mean of the values in the highest level (top 10%) is calculated as a high standard value. A mean of the values in the lowest level is calculated as a low standard value. The low standard value is set as 0, and the high standard value is set as 1, such that all the values of the normalization target are ranged from 0 to 1. That is to say, the values of the eye movement ratio M, the blink count B, the low-frequency power ratio $R_{P0-4}$, the high-frequency power ratio $R_{P13-22}$, the alpha ratio $R_\alpha$, the spindle ratio $R_S$, the delta ratio $R_\delta$ and the mean amplitude of EOG signal are then ranged from 0 to 1.

Afterwards, some smoothing rules can be used to increase the accuracy as shown in Table 2.

TABLE 2

Table of Smoothing rules.

| Number | Smoothing rules |
|---|---|
| 1 | Any REM before the very first appearance of S2 is replaced with S1 |
| 2 | Wake, REM, S2 → Wake, S1, S2 |
| 3 | S1, REM, S2 → S1, S1, S2 |
| 4 | S2, S1, S2 → S2, S2, S2 |
| 5 | S2, SWS, S2 → S2, S2, S2 |
| 6 | S2, REM, S2 → S2, S2, S2 |
| 7 | SWS, S2, SWS → SWS, SWS, SWS |
| 8 | REM, Wake, REM → REM, REM, REM |

TABLE 2-continued

Table of Smoothing rules.

| Number | Smoothing rules |
|---|---|
| 9 | REM, S1, REM → REM, REM, REM |
| 10 | REM, S2, REM → REM, REM, REM |

Figure 5A:
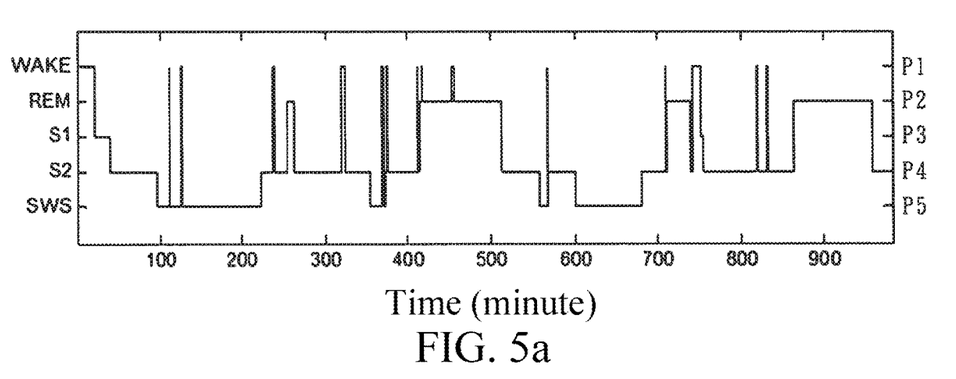
FIG. 5a a diagram illustrating a determination result of sleep staging through a manual approach by experts.
Figure 5B:
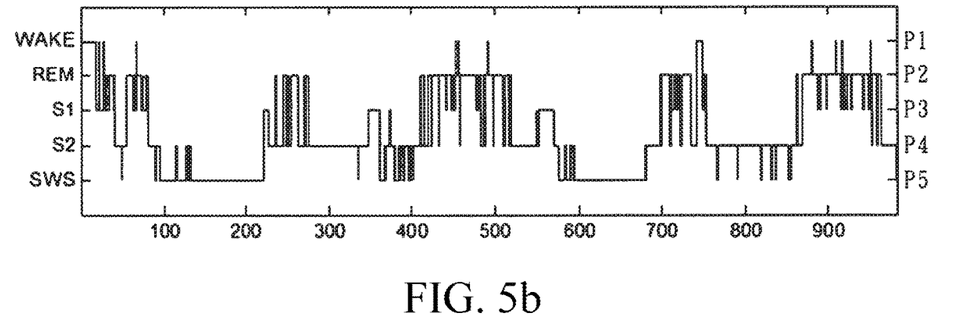
FIG. 5b is a diagram illustrating a determination result of sleep staging through the EOG-based sleep staging method of an embodiment of the invention without smoothing.
Figure 5C:
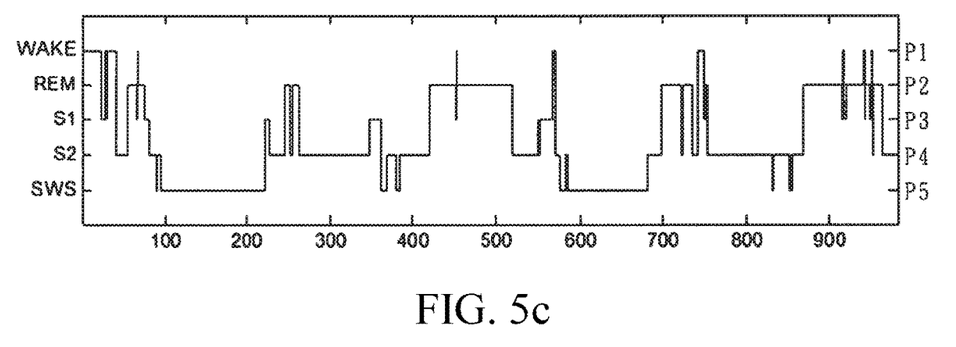
FIG. 5c is a diagram illustrating a determination result of sleep staging through the EOG-based sleep staging method of an embodiment of the invention with smoothing.

Referring to FIGS. 5a, 5b, and 5c, FIG. 5a a diagram illustrating a determination result of sleep staging through a manual approach by experts, FIG. 5b is a diagram illustrating a determination result of sleep staging through the EOG-based sleep staging method of an embodiment of the invention without smoothing, and FIG. 5c is a diagram illustrating a determination result of sleep staging through the EOG-based sleep staging method of an embodiment of the invention with smoothing. As shown in FIG. 5a and FIG. 5B, the difference between the determination of the EOG-based sleep staging method of the invention without smoothing and the determination through manual approach by experts is not large. As shown in FIG. 5a and FIG. 5c, the difference between the determination of the EOG-based sleep staging method of the invention with smoothing and the determination through manual approaches by experts is similar, and the consistency between the two is up to 83.08%. The calculation of the consistency is: the percentages of all the 30-epoches that the determination by the EOG-based sleep staging method of the embodiment of the invention is equal to that of the manual approach.

Accordingly, the EOG-based sleep tagging method of the embodiment of the invention can increase the scoring accuracy for sleep staging, and it can be applied to fields such as clinical medicine and home health care.

In addition, the EOG-based sleep staging method of the embodiment of the invention could be implemented as computer programs (e.g. sleep staging program) by program languages such as C++, Java, etc. Peoples in the art should be able to write program code to generate a computer program product storing the program. When a computer loads the program and execute it, the method embodiment of the invention is performed.

In addition, the computer program product can be stored in a non-transitory computer readable recording medium such as any type of memory, memory card, hard disk, optical disk, pen drive, etc. When a computer loads the program and execute it, the EOG-based sleep staging method of the invention is performed as the base of co-operation of hardware and software in a computer system of the present invention.

In addition, an electronic device is provided. The electronic device may be a device having functions of data processing. For example, the electronic device may be computer, smart phone, etc., for executing an application and performing the EOG-based sleep staging method.

As the technical means described above, the EOG-based sleep staging method, the non-transitory computer readable recording medium, and the electronic device described above have features of: reading to-be-test data, wherein the to-be-test data includes a EOG signal having a variation depending on time of the EOG signal generated by a user during a sleep process; acquiring multiple eye movement characteristics according to the variation of the EOG signal during an epoch, wherein the eye movement characteristics include an eye movement ratio, a blink count, a low-frequency power ratio, a high-frequency power ratio, an alpha ratio, a spindle ratio, a delta ratio and an mean amplitude of the EOG signal; determining, by the decision three, a sleep state of the epoch is a WAKE stage, a non-rapid-eye-movement (REM) stage, a S1 stage a S2 stage or a slow-wave-sleep (SWS) stage according to the eye movement characteristics. Accordingly, the embodiments of the invention can increase the scoring accuracy of sleep staging, and therefore the advantage of "easy to get accurate sleep staging result" is achieved, and can be applied to fields such as clinical medicine and home health care.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An electrooculograppy(EOG)-based sleep staging method for a processor, the method comprising:
    a preparing step by a polysomnography, reading to-be-test data, wherein the to-be-test data comprises an EOG signal having a variation depending on time of the EOG signal generated by a user during a sleep process;
    an acquiring step by the processor, acquiring a plurality of eye movement characteristics according to the variation of the EOG signal during an epoch comprising a plurality of segments, wherein the eye movement characteristics comprise an eye movement ratio, a blink count, a low-frequency power ratio, a high-frequency power ratio, an alpha ratio, a spindle ratio, a delta ratio and a mean amplitude of the EOG signal, wherein the eye movement ratio is a ratio of a number of eye moving segments to a number of the segments in the epoch, the low-frequency power ratio is a ratio of a power of 0-4 hertz of a frequency-domain signal to 0-30 hertz of the frequency-domain signal in the epoch, the high-frequency power ratio is a ratio of a power of 13-22 hertz of the frequency-domain signal to 0-30 hertz of the frequency-domain signal in the epoch, the alpha ratio is a ratio of a number of alpha segments to the number of the segments in the epoch, the spindle ratio is a ratio of a number of spindle segments to the number of the segments in the epoch, and the delta ratio is a ratio of a number of slow-wave-sleep segments to the number of the segments in the epoch;
    a determining step by the processor, determining that a sleep state of the epoch is a WAKE stage, a rapid eye movement (REM) stage, a S1 stage, a S2 stage or a slow wave sleep (SWS) stage according to the plurality of eye movement characteristics by a decision tree comprising:
        a first node, determining whether the eye movement ratio is greater than a first threshold, and performing a second node if yes, and performing a third node if not;
        the second node, determining whether the delta ratio is greater than a second threshold and the high-frequency power ratio is less than a third threshold, and determining that the sleep state is the SWS stage if yes, and determining that the sleep state is the S2 stage if not;
        the third node, determining whether the eye movement ratio is greater than a fourth threshold, and performing a fourth node if yes, and performing a fifth node if not, wherein the fourth threshold is less than the first threshold;
        the fourth node, determining whether the spindle ratio is greater than a fifth threshold and the low-frequency power ratio is less than a sixth threshold, and performing a sixth node if yes, and determining that the sleep state is the REM stage if not;
        the fifth node, determining whether the alpha ratio is greater than a seventh threshold and the blink count is greater than an eighth threshold, and determining that the sleep state is the WAKE stage if yes, and performing a seventh node if not;
        the sixth node, determining whether the mean amplitude of the EOG signal is greater than a ninth threshold, and determining that the sleep state is the S1 stage if yes, and determining that the sleep state is the S2 stage if not; and
        the seventh node, determining whether the alpha ratio is greater than a tenth threshold, and determining that the sleep state is the S2 stage if yes, and determining that the sleep state is the REM stage if not, wherein the tenth threshold is less than the seventh threshold; and
    applying a plurality of smoothing rules to the EOG signal, wherein the smoothing rules comprise:
        each REM stage before a very first appearance of the S2 stage is replaced with the S1 stage;
        a sequence of the WAKE stage, the REM stage, and the S2 stage is replaced with a sequence of the WAKE stage, the S1 stage, and the S2 stage;
        a sequence of the S1 stage, the REM stage, and the S2 stage is replaced with a sequence of the S1 stage, the S1 stage, and the S2 stage;
        a sequence of the S2 stage, the S1 stage, and the S2 stage is replaced with a sequence of the S2 stage, the S2 stage, and the S2 stage;
        a sequence of the S2 stage, the SWS stage, and the S2 stage is replaced with a sequence of the S2 stage, the S2 stage, and the S2 stage;
        a sequence of the S2 stage, the REM stage, and the S2 stage is replaced with a sequence of the S2 stage, the S2 stage, and the S2 stage;
        a sequence of the SWS stage, the S2 stage, and the SWS stage is replaced with a sequence of the SWS stage, the SWS stage, and the SWS stage;
        a sequence of the REM stage, the WAKE stage, and the REM stage is replaced with a sequence of the REM stage, the REM stage, and the REM stage;
        a sequence of the REM stage, the S1 stage, and the REM stage is replaced with a sequence of the REM stage, the REM stage, and the REM stage; and
        a sequence of the REM stage, the S2 stage, and the REM stage is replaced with a sequence of the REM stage, the REM stage, and the REM stage.

2. The EOG-based sleep staging method of claim 1, wherein the first threshold is ranged from 0.55 to 0.65, the second threshold is ranged from 0.19 to 0.25, the third threshold is ranged from 0.01 to 0.05, the fourth threshold is ranged from 0.3 to 0.5, the fifth threshold is ranged from 0.2 to 0.4, the sixth threshold is ranged from 0.12 to 0.19, the seventh threshold is ranged from 0.3 to 0.5, the eighth threshold is ranged from 4 to 6, the ninth threshold is ranged from 0.25 to 0.35, and the tenth threshold is ranged from 0.12 to 0.19.

3. The EOG-based sleep staging method of claim 1, wherein before calculating the correlation coefficient, the method further comprises:
   performing a fourth-order 0-6 hertz band pass filter on the left EOG signal and the right EOG signal.

4. The EOG-based sleep staging method of claim 1, wherein the EOG signal comprises a left EOG signal and a right EOG signal, and the method further comprises:
   selecting one of the left EOG signal and the right EOG signal as a sampling signal, calculating an EOG velocity according to the sampling signal, and counting times of the EOG velocity being greater than a threshold in the epoch as the blink count.

5. The EOG-based sleep staging method of claim 4, wherein the EOG velocity is calculated by a formula:

$$V = \frac{dEOG}{dt} \approx \frac{EOG((k+1)\cdot T) - EOG(k\cdot t)}{T},$$

wherein V is the EOG velocity;

$$\frac{dEOG}{dt}$$

is a first derivative function of the sampling signal with respect to time t; T is a sampling period; $EOG(k\cdot T)$ is the sampling signal in a $k^{th}$ sampling period; and $EOG((k+1)\cdot T)$ is the sampling signal in a $(k+1)^{th}$ sampling period.

6. The EOG-based sleep staging method of claim 1, wherein the EOG signal comprises a left EOG signal and a right EOG signal, and the method further comprises:
   selecting one of the left EOG signal and the right EOG signal as a sampling signal, and transforming the sampling signal into the frequency-domain signal.

7. The EOG-based sleep staging method of claim 1, wherein the EOG signal comprises a left EOG signal and a right EOG signal, and the method further comprises:
   calculating a mean of absolute amplitudes of the left EOG signal and right EOG signal as the mean amplitude of the EOG signal.

8. The EOG-based sleep staging method of claim 1, wherein a normalization step is performed between the acquiring step and the determining step, and the normalization step comprises:
   sequentially taking the eye movement ratio, the blink count, the low-frequency power ratio, the high-frequency power ratio, the alpha ratio, the spindle ratio, the delta ratio and the mean amplitude of the EOG signal as a normalization target;
   sorting values of the normalization target, uniformly dividing the values into ten levels, calculating a mean of the values in a highest level of the levels as a high standard value, and calculating a mean of the values in a lowest level of the levels as a low standard value; and
   setting the low standard value as 0, and setting the high standard value as 1, such that all the values of the normalization target are ranged from 0 to 1.

9. A non-transitory computer readable recording medium storing a program, wherein the program is configured to be loaded and executed by a computer to perform the method of claim 1.

10. An electronic device configured to load a program stored in a computer readable recording medium for performing the method of claim 1.

* * * * *